United States Patent

Pfeffinger et al.

(10) Patent No.: US 6,790,995 B2
(45) Date of Patent: Sep. 14, 2004

(54) PREPARATION OF PRIMARY AND SECONDARY AMINES FROM NITRILES

(75) Inventors: Joachim Pfeffinger, Ludwigshafen (DE); Michael Hüllmann, Bensheim (DE); Arthur Höhn, Kirchheim (DE); Frank Funke, Mannheim (DE); Frank Ohlbach, Düsseldorf (DE); Till Gerlach, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/033,912

(22) Filed: Jan. 3, 2002

(65) Prior Publication Data

US 2002/0091194 A1 Jul. 11, 2002

(30) Foreign Application Priority Data

Jan. 5, 2001 (DE) .......................... 101 00 313

(51) Int. Cl.$^7$ ............................................. C07C 209/48
(52) U.S. Cl. ....................................... 564/490; 564/493
(58) Field of Search .................................. 564/490, 493

(56) References Cited

U.S. PATENT DOCUMENTS

| 5,101,075 A | 3/1992 | Käsbauer et al. ............ 564/490 |
| 5,894,074 A | 4/1999 | Fuchs et al. ................. 564/490 |
| 6,525,233 B1 * | 2/2003 | Pfeffinger et al. ............ 564/490 |

FOREIGN PATENT DOCUMENTS

| DE | 39 35 641 | 5/1991 |
| EP | 0 869 113 | 10/1998 |
| WO | WO 99/32429 | 7/1999 |

OTHER PUBLICATIONS

Collection of Czechoslovak Chemical Communications (2000), 65 (11), p. 1805–1819.*

* cited by examiner

Primary Examiner—Brian Davis
(74) Attorney, Agent, or Firm—Keil & Weinkauf

(57) ABSTRACT

Mixtures of primary amines of the formula (I)

$$X\text{—}CH_2\text{—}NH_2 \quad (I)$$

and secondary amines of the formula (II)

$$(X\text{—}CH_2\text{—})_2NH \quad (II)$$

where
X is $C_{1-20}$-alkyl, $C_{2-20}$-alkenyl or $C_{3-8}$-cycloalkyl which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl are prepared by reacting nitriles of the formula (III)

$$X\text{—}CN \quad (III)$$

with hydrogen at from 50 to 250° C. and pressures of from 5 to 350 bar in the presence of a Pd-containing catalyst comprising, based on the total weight of the catalyst, from 0.1 to 10% by weight of Pd on a support.

8 Claims, No Drawings

PREPARATION OF PRIMARY AND SECONDARY AMINES FROM NITRILES

The present invention relates to a process for preparing mixtures of primary and secondary amines from nitriles over a palladium catalyst.

Processes for preparing amines from nitriles over particular palladium catalysts are known.

DEA-39 35 641 describes the preparation of amines from 3-(dimethylamino)propionitrile (DMAPN). Products formed are bis(3-(dimethylamino)propyl)amine (bis-DMAPA) and tris(3-(dimethylamino)propyl)amine (tris-DMAPA). The reaction is carried out over palladium on aluminum oxide as catalyst. The proportion of bis-DMAPA is not more than 32%.

EP-A-0 869 113 relates to a process for preparing tertiary amines from nitriles and secondary amines. Here, secondary amines are reacted in the presence of hydrogen over a catalyst comprising 0.9% of Pd and 0.1% of Pd on zirconium oxide as support.

WO 99/32429 relates to a process for preparing secondary amines from nitriles and primary amines. The reaction is carried out in the presence of hydrogen likewise over the abovementioned catalyst comprising 0.9% of Pd and 0.1% of Pt on zirconium oxide.

It is an object of the present invention to provide a process for preparing mixtures of primary amines and secondary amines by reaction of nitriles with hydrogen in the presence of catalysts.

In particular, mixtures of primary and symmetrical secondary amines are to be prepared.

We have found that this object is achieved by a process for preparing mixtures of primary amines of the formula (I)

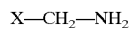

$$X-CH_2-NH_2 \qquad (I)$$

and secondary amines of the formula (II)

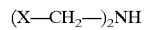

$$(X-CH_2-)_2NH \qquad (II)$$

where

X is $C_{1-20}$-alkyl, $C_{2-20}$-alkenyl or $C_{3-8}$-cycloalkyl which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl by reacting nitriles of the formula (III)

$$X-CN \qquad (III)$$

with hydrogen at from 50 to 250° C. and pressures of from 5 to 350 bar in the presence of a Pd-containing catalyst comprising, based on the total weight of the catalyst, from 0.1 to 10% by weight of Pd on a support.

The catalyst preferably further comprises from 0.1 to 10% by weight of at least one additional metal selected from among groups IB and VIII of the Periodic Table, cerium and lanthanum.

According to the present invention, it has been found that the use of a catalyst as defined above for reacting nitriles with hydrogen to give mixtures of primary and secondary amines can lead to an increased operating life or long-term stability of the catalyst.

The catalysts used according to the present invention contain, based on the total weight of the catalyst, from 0.1 to 10% by weight, preferably from 0.1 to 5% by weight, particularly preferably from 0.2 to 1% by weight, of palladium.

In addition, they may farther comprise, based on the total weight of the catalyst, from 0.1 to 10% by weight, preferably from 0.1 to 5% by weight, particularly preferably from 0.2 to 1% by weight, of at least one additional metal selected from among groups IB and VIII of the Periodic Table of the Elements, cerium and lanthanum. One further metal or a mixture of a plurality of further metals can be used. Preference is given to using copper, platinum and mixtures thereof, particularly preferably platinum. Particular preference is given to a catalyst containing from 0.2 to 1% by weight of palladium and from 0.2 to 1% by weight of platinum, in particular from 0.3 to 0.5% by weight of palladium and from 0.3 to 0.5% by weight of platinum, based on the total weight of the catalyst.

Particular preference is given to a catalyst comprising about 0.4% by weight of Pd and about 0.4% by weight of Pt, based on the total weight of the catalyst, on $ZrO_2$ as support.

The catalyst preferably comprises Pd and Pt as only active components. The catalyst particularly preferably consists of Pd and Pt on the support. Here, Pd and Pt are preferably present in approximately or exactly equal amounts, based on the weight.

All known, suitable supports can be used as supports. For example, the support is selected from among activated carbon, silicon carbide and metal oxides. Preferred metal oxides are aluminum oxide, silicon dioxide, titanium dioxide, zirconium dioxide, zinc oxide, magnesium oxide or mixtures thereof, which may optionally be doped with alkali metal oxides and/or alkaline earth metal oxides. Particular preference is given to using γ-aluminum oxide, silicon dioxide, zirconium dioxide or titanium oxide or mixtures thereof, in particular $ZrO_2$. The supports used can have any shape; for example they can be used as extrudates, pellets or tablets. The catalysts can be produced by generally known methods, for example by impregnating the support with solutions of compounds of the metals used. Palladium can be applied, for example, by impregnating the support with solutions of $PdCl_2$ or $Pd(NO_3)_2$.

The supports can, for example, be coated with metal precursors. Suitable metal precursors are metal salts such as nitrates, nitrosyl nitrates, halides, carbonates, carboxylates, acetylacetates, chloro complexes, nitrito complexes and amine complexes. Preference is given to nitrates, chlorides, chloro complexes and amine complexes. Application is preferably carried out by coprecipitation or joint impregnation. The metal precursors can be applied simultaneously or in succession. The order in which the active components are applied can be chosen freely.

Further methods of producing the catalysts used according to the present invention are known to those skilled in the art and include vapor deposition, sputtering and coprecipitation.

The surface area, the pore volume and the pore size distribution of the catalyst are not critical within wide ranges.

The process of the present invention is carried out at from 50 to 200° C., preferably from 90 to 170° C. particularly preferably from 120 to 160° C., and pressures of from 5 to 300 bar, preferably from 50 to 250 bar, particularly preferably from 70 to 210 bar, batchwise or preferably continuously in pressure apparatuses such as autoclaves or preferably in a tube reactor. The pressure is preferably the hydrogen pressure in the reactor. When using a tube reactor, the catalyst employed can also be present as a fixed-bed catalyst.

The reaction is preferably carried out in the liquid phase in the upflow or downflow mode, particularly preferably in the upflow mode. In particular, preference is given to carrying out the reaction without the use of ammonia.

The space velocity over the catalyst, based on the nitrile used, is preferably from 0.1 to 2 kg/(l·h), in particular about 0.1 kg/(l·h). Part of the liquid output from the reactor can be recirculated to the reaction. The reaction is preferably carried out with recirculation of liquid output from the reactor in an amount of from 1 to 20 kg/($l_{cat}$·h), in particular from 5 to 10 kg/($l_{cat}$·h).

The process of the present invention can be carried out in the absence of solvents or in solvents such as water, methanol, ethanol, tetrahydrofuran methyl tert-butyl ether or N-methylpyrrolidone, The nitrile of the formula (III) may be dissolved in the solvent. The solvent can also be fed separately into the reactor at any point. Preference is given to candying out the reaction in the absence of solvents.

The amines of the formulae (I) and (II) obtained in the process of the present invention can be separated from the reaction mixture and purified in a manner known per se, for example by distillation.

It is, for example, possible to obtain a stream comprising pure secondary amine and a stream comprising primary amine by rectification, with the stream comprising the primary amine being returned to the synthesis.

According to the present invention, the primary amines of the formula (I) and the secondary amines of the formula (II) are preferably formed in a weight ratio of from 10:1 to 1:10, more preferably from 2 to 4:5. The amounts of tertiary amines formed are preferably very small; in particular, preferably no tertiary amines are formed. The amount of tertiary amines formed is preferably less than 15% by weight, particularly preferably less than 10% by weight, based on the output from the reactor (without solvent).

In the process of the present invention, nitrites of the formula (III) are reacted.

$$X\text{—}CN \quad (III)$$

X is $C_{1-20}$-alkyl, $C_{2-20}$-alkenyl or $C_{3-8}$-cycloalkyl which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkoxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$-alkylamino, halogen, mercapto, $C_{2-20}$-alkenyloxy, $C_{3-8}$-cycloalkoxy, aryloxy and/or $C_{2-8}$-alkoxycarbonyl.

X is preferably $C_{1-12}$—, particularly preferably $C_{1-8}$—, in particular $C_{1-6}$—, especially $C_{1-4}$-alkyl which may be branched or unbranched and is preferably unbranched. Examples are unbranched radicals made up of 1, 2, 3, 4. 5, 6, 7, 8, 9, 10, 11, 12, 13, 14, 15, 16, 17, 13, 19, 20 methylene units, C(C)—C—C, C—C(C)—C, C—C(C)$_2$—C as structural units. Preferred structural units are C, C—C, C—C—C, C—C—C—C, C—C—C—C—C—C, C—C(C)—C, C—C(C)—C—C, C—C—C(CN)—C—C—C, particularly preferably C, C—C, C—C—C, C—C—C—C.

X can, as indicated above, be substituted. In this case, the number of substituents may be up to the number of replaceable hydrogen atoms in X. Regardless of the type of radical, from 1 to 5, preferably from 1 to 3, in particular 0, 1 or 2, substituents may be present. Possible substituents are:

$C_{1-20}$-alkoxy, preferably $C_{1-8}$-alkoxy such as in methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy such as methoxy, ethoxy, n-propoxy, isopropoxy, n-butoxy, isobutoxy, sec-butoxy and tert-butoxy, hydroxy, $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 2-hydroxy-2-propyl and 3-hydroxy-n-propyl, amino, $C_{1-20}$-alkylamino, preferably $C_{1-8}$-alkylamino, particularly preferably $C_{1-4}$-alkylamino such as methylamino, or corresponding aminoalkyl, 1-aminoethyl, 2-aminoethyl, 2-amino-n-propyl and 3-amino-n-propyl, $C_{2-20}$-dialkylamino, preferably $C_{2-12}$-dialkylamino, particularly preferably $C_{2-8}$-dialkylamino such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, n-(1-methylethyl)-N-(1-methylpropyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, n-(1,1-dimethylethyl)-N-(1-methylpropyl)amino and N-(1,1-dimethylethyl)-N-(2-methylpropyl)amino, $C_{3-12}$-azacycloalkyl, preferably $C_{3-8}$-azacycloalkylamino, particularly preferably $C_{5-8}$-azacycloalkyl such as pyrrolidine, piperidine, azepane, piperazine, N-alkylpiperazine and morpholine, $C_{3-8}$-cycloalkylamino such as cyclopropylamino, cyclobutylamino, cyclopentylamino, cyclohexylamino, cycloheptylamino and cyclooctylamino, preferably cyclopentylamino, cyclohexylamino and cyclooctylamino, particularly preferably cyclopentylamino and cyclohexylamino, $C_{3-8}$-dicycloalkylamino, arylamino such as phenylamino, 1-naphthylamino and 2-naphthylamino, preferably phenylamino, aryl-$C_{1-8}$-alkylamino, preferably phenyl-$C_{1-8}$-alkylamino, particularly preferably phenyl-$C_{1-4}$-alkylamino such as phenylmethylamino and phenylethylamino, halogen, preferably fluorine, chlorine and bromine, particularly preferably fluorine and chlorine, mercapto, $C_{2-20}$-oxacycloalkyl, preferably $C_{2-8}$-oxacycloalkyl, particularly preferably $C_{2-8}$-oxacycloalkyl such as 2-tetrahydrofuranyl, 3-tetrahydrofuranyl, 2-furanyl and 3-furanyl, $C_{3-8}$-cycloalkoxy such as cyclopropoxy, cyclobutoxy, cyclopentoxy, cyclohexyl, cycloheptoxy and cyclooctoxy, preferably cyclopentoxy, cyclohexoxy, particularly preferably cyclopentoxy and cyclohexoxy, aryloxy such as phenoxy, 1-naphthoxy and 2-naphthoxy, preferably phenoxy.

0, 1 or 2 OH or $C_{2-12}$—, preferably $C_{2-6}$—, in particular $C_{2-4}$-dialkylamino substituents are preferably present. In particular, the substituents are dimethylamino or OH.

Preferred nitriles of the formula (III) are acetonitrile, propionitrile, isopropionitrile, butyronitrile, valeronitrile, pentenenitrile, retenenitrile, 3-hydroxypropionitrile, 3-methoxypropionitrile, 3-ethoxypropionitrile, 3-propoxypropionitrile, 3-isopropoxypropionitrile, 3-cyclohexoxypropionitrile, 2-methyl-3-hydroxypropionitrile, 3-methoxy-2-methylpropionitrile, 3-ethoxy-2-methylpropionitrile, 2-methyl-3-propoxypropionitrile, 3-isopropoxy-2-methylpropionitrile, 3-cyclohexoxy-2-methylpropionitrile, 3-methyl-3-hydroxypropionitrile, 3-methoxy-3-methylpropionitrile, 3-ethoxy-3-methylpropionitrile, 3-methyl-3-propoxypropionitrile, 3-isopropoxy-3-methylpropionitrile, 3-cyclohexoxy-3-methylpropionitrile, 3-aminopropionitrile, 3-methylaminopropionitrile, 3-dimethylaminopropionitrile, 3-methylaminopropionitrile, 3-diethylaminopropionitrile, 3-propylaminopropionitrile, 3-dipropylaminopropionitrile, 3-isopropylaminopropionitrile, 3-diisopropylaminopropionitrile, 3-cyclohexylaminopropionitrile, 3-dicyclohexylaminopropionitrile, N-(cyanoethyl)-N-methylaniline. Particular preference is given to 3-hydroxypropionitrile, 3-methoxypropionitrile, 3-dimetylaminopropionitrile, 3-diethylaminopropionitrile, 3-cyclohexylaminopropionitrile and 3-methylaminopropionitrile, in particular biscyanoethyl ether, biscyanoethylamine, N-methylbiscyanoethylamine, N-ethylbiscyanoethylamine, N-n-propylbiscyanoethylamine, polyisobutylenenitrile, N-polyisobutyleneaminopropionitrile, tricyanoethylamine, 5-aminovaleronitrile, 5-methylaminovaleronitrile, 5-dimethylaminovaleronitrile, 6-aminocapronitrile, 6-methylaminocapronitrile, 6-dimethylaminocapronitrile, 5-amino-4-methylvaleronitrile, 5-methylamino-4-methylvaleronitrile, 5-dietlylamino-4-methylvaleronitrile, 5-ethylamino-4-methylvaleronitrile, 5-diethylamino-4-methylvaleronitrile, 5-amino-2-methylvaleronitrile, 5-methylamino-2-methylvaleronitrile, 5-dimethylamino-2-valeronitrile, 5-ethylamino-2-methylvaleronitrile, 5-diethylamino-2-methylvaleronitrile, 4-cyanosuberonitrile, acrylonitrile.

Particular preference is given to adiponitrile, 3-dimethylaminopropionitrile (DMAPN) and 3-hydroxypropionitrile, especially DMAPN.

The amine mixtures, preferably DMAPA and bis-DMAPA are hardeners for epoxy resins, catalysts for polyurethanes, intermediates for preparing quaternary ammonium compounds, plasticizers, corrosion inhibitors, textile assistants, dyes and emulsifiers. Multiply functionalized tertiary amines are also employed for producing synthetic resins ion exchangers, pharmaceuticals, crop protection agents and pesticides.

The invention is illustrated by the following example.

EXAMPLE

An electrically heated tube reactor having an internal diameter of 30 mm, a total length of 2.0 m and fitted with a central thermocouple having a diameter of 12 mm is charged with a mixture of 570 g (~500 ml) of catalyst and 450 ml of stainless steel packing elements. The catalyst comprises 0.4% by weight of Pt and 0.4% by weight of Pd on zirconiumn dioxide as support material and is in the form of rings having a diameter of 7 mm, a thickness of 3 mm and a hole diameter of 3 mm.

Prior to the reaction the catalyst is reduced at 160° C. by means of pure hydrogen under atmospheric pressure and for a period of 12 hours.

500 g/h of 3-(dimethylamino)propionitrile (DMAPN), 4.0 kg/h of liquid output from the reactor and 0.38 standard m³/h of hydrogen are passed through the reactor in cocurrent from the bottom upward. The starting materials are heated to 140° C. upstream of the reactor. The reactor is maintained at 140° C. and a total pressure of 80 bar.

The mixture leaving the reactor is cooled, part of the liquid is recirculated to the reactor inlet and the remainder is depressurized to atmospheric pressure. Analysis by means of gas chromatography found 50% by weight of bis(3-dimethylaminopropyl)amine (bis-DMAPA), 30% by weight of 3-dimethylaminopropylamine (DMAPA), 3.0% by weight of DMAPN and 17% by weight of various by-products in the output from the reactor. The conversion of DMAPN was thus 97%.

2300 g of the liquid output from the reactor were subsequently distilled batchwise in a laboratory distillation using a column containing random packing (20 theoretical plates) at a pressure at the top of 30 mbar (abs.) and a reflux ratio of 5:1. This gave one fraction of 730 g (going over at 45° C.) containing 90.0% by weight of DMAPA, 5.5% of DMAPN and 4.5% of by-products and also a second fraction of 960 g (going over at 125° C.) containing 99.3% by weight of bis-DMAPA.

We claim:

1. A process for preparing mixtures of primary amines of the formula (I)

X—$CH_2$—$NH_2$     (I)

and secondary amines of the formula (II)

(X—$CH_2$—)$_2$NH     (II)

where

X is $C_{1-20}$-alkyl, $C_{2-20}$-alkenyl or $C_{3-8}$-cycloalkyl which may be unsubstituted or substituted by $C_{1-20}$-alkyl, $C_{3-8}$-cycloalkyl, $C_{4-20}$-alkylcycloalkyl, $C_{4-20}$-cycloalkylalkyl, $C_{2-20}$-alkloxyalkyl, $C_{6-14}$-aryl, $C_{7-20}$-alkylaryl, $C_{7-20}$-aralkyl, $C_{1-20}$-alkoxy, hydroxy, $C_{1-20}$-hydroxyalkyl, amino, $C_{1-20}$-alkylamino, $C_{2-20}$-dialkylamino, $C_{2-12}$-alkenylamino, $C_{3-8}$-cycloalkylamino, arylamino, diarylamino, aryl-$C_{1-8}$- alkylamino, halogen, mercapto, $C_{2-20}$-alkenyloxy, $C_{3-8}$-cycloalkoxy, aryloxy and/or $C_{2-8}$-alkoxycarbonyl by reacting nitriles of the formula (III)

$$X-CN \qquad (III)$$

with hydrogen at from 50 to 250° C. and pressures of from 5 to 350 bar in the presence of a Pd-containing catalyst comprising, based on the total weight of the catalyst, from 0.1 to 10% by weight of Pd on a support, wherein the catalyst further comprises from 0.1 to 10% by weight of at least one additional metal selected from among groups IB and VIII of the Periodic Table, cerium and lanthanum.

2. A process as claimed in claim 1, wherein the catalyst contains from 0.2 to 1% by weight of Pd and from 0.2 to 1% by weight of Pt.

3. A process as claimed in claim 1, wherein the support is selected from among activated carbon, silicon carbide and metal oxides.

4. A process as claimed in claim 3, wherein the support is $ZrO_2$.

5. A process as claimed in claim 1, wherein X is linear $C_{1-6}$-alkyl having up to 2 substituents.

6. A process as claimed in claim 5, wherein the substituents are $C_{2-12}$-dialkylamino or OH.

7. A process as claimed in claim 6, wherein the nitrile of the formula (III) is 3-(dimethylamino)propionitrile (DMAPN) which is converted into a mixture of bis(3-(dimethylamino)propyl)amine and 3-(dimethylamino) propylamine.

8. A process as claimed in claim 1, wherein the primary amines of the formula (I) and the secondary amines of the formula (II) are formed in a weight ratio of from 10:1 to 1:10.

* * * * *